(12) United States Patent
Maddalo et al.

(10) Patent No.: US 6,454,787 B1
(45) Date of Patent: *Sep. 24, 2002

(54) COLLAGEN HEMOSTATIC FOAM

(75) Inventors: Francis B. Maddalo, Needham; Mark V. Iampietro, Ashland, both of MA (US); Stephen N. Eldridge, Cranston; Robert D. Torgerson, Wakefield, both of RI (US)

(73) Assignee: C. R. Bard, Inc., Murray Hill, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/209,600

(22) Filed: Dec. 11, 1998

(51) Int. Cl.[7] .............................................. A61B 17/08
(52) U.S. Cl. ............................... 606/214; 128/DIG. 8; 106/122; 514/801; 424/423
(58) Field of Search ................... 606/214; 128/DIG. 8; 106/122, 124.1, 160.1; 541/21, 801; 424/422, 423

(56) References Cited

U.S. PATENT DOCUMENTS

| | | |
|---|---|---|
| 505,148 A | 9/1893 | Weaver |
| 2,598,608 A | 5/1952 | Salo et al. .................. 260/117 |
| 2,637,321 A | 5/1953 | Cresswell ................ 128/335.5 |
| 2,654,752 A | 10/1953 | Rhodehamel, Jr. et al. ........................ 260/239.1 |
| 2,919,999 A | 1/1960 | Reissmann et al. ......... 106/161 |
| 2,920,000 A | 1/1960 | Hochstadt et al. .......... 106/161 |
| 3,114,235 A | 12/1963 | Griset, Jr. ..................... 57/157 |
| 3,114,591 A | 12/1963 | Nichols et al. ................ 18/54 |
| 3,114,593 A | 12/1963 | Griset et al. .................... 18/54 |
| 3,157,524 A | 11/1964 | Artandi |
| 3,293,237 A | 12/1966 | Wiegand ................. 260/123.7 |
| 3,366,440 A | 1/1968 | Nuwayser ..................... 8/115.6 |
| 3,502,534 A | 3/1970 | Griset, Jr. ..................... 156/344 |
| 3,520,402 A | 7/1970 | Nichols |
| 3,587,586 A | 6/1971 | Kronenthal .................. 128/334 |
| 3,625,811 A | 12/1971 | Okamura ........................ 162/2 |
| 3,742,955 A | 7/1973 | Battista et al. .......... 128/334 R |

(List continued on next page.)

FOREIGN PATENT DOCUMENTS

| | | |
|---|---|---|
| DE | 1469075 | 12/1968 |
| EP | 083 868 | 12/1982 |
| EP | 0 310 623 | 12/1987 |

(List continued on next page.)

OTHER PUBLICATIONS

Braun Product Insert on Web Page for Osteovit® collagen matrix for filling bone defects (one page).
Braun Product Insert on Web Page for Lyostrypt® local haemostatic agent (one page).
Bloom W et al. *A Textbook of Histology;* Ninth Ed; WB Saunders, Philadelphia, 1970; see pp. 223–224.

(List continued on next page.)

*Primary Examiner*—Gary Jackson
(74) *Attorney, Agent, or Firm*—Wolf, Greenfield & Sacks, P.C.

(57) ABSTRACT

A hemostatic device formed of collagen particles and methods for producing and using the hemostatic device to control bleeding are provided. The collagen particles of the hemostatic device have a hemostatic activity that is equivalent to the hemostatic activity of the collagen particles from which the hemostatic device is formed. More preferably, the hemostatic devices are formed of Avitene® flour and the collagen particles of the hemostatic devices of the invention have a hemostatic activity equivalent to the hemostatic activity of Avitene® flour. The hemostatic devices optionally include hemostatic agents and/or therapeutic agents, to further promote hemostasis and wound healing.

45 Claims, 2 Drawing Sheets

U.S. PATENT DOCUMENTS

| | | | |
|---|---|---|---|
| 3,810,472 A | | 5/1974 | Aldinger ..................... 128/287 |
| 3,823,212 A | | 7/1974 | Chvapil ....................... 264/49 |
| 3,896,814 A | | 7/1975 | Vivien et al. ............ 128/335.5 |
| 4,016,877 A | | 4/1977 | Cruz, Jr. et al. ............ 128/156 |
| 4,066,083 A | | 1/1978 | Ries |
| 4,097,234 A | | 6/1978 | Sohde et al. ..................... 8/94 |
| 4,140,537 A | | 2/1979 | Luck et al. ................. 106/155 |
| 4,148,664 A | | 4/1979 | Cruz, Jr. ..................... 106/161 |
| 4,193,813 A | | 3/1980 | Chavpil ....................... 106/122 |
| 4,233,360 A | * | 11/1980 | Luck et al. ................. 428/310 |
| 4,238,480 A | | 12/1980 | Sawyer ....................... 424/177 |
| 4,271,070 A | * | 6/1981 | Miyata .................... 260/123.7 |
| 4,273,705 A | | 6/1981 | Kato ....................... 260/123.7 |
| 4,319,363 A | | 3/1982 | Ketharanathan ................ 3/1.4 |
| 4,390,519 A | | 6/1983 | Sawyer ....................... 424/28 |
| 4,404,033 A | | 9/1983 | Steffan ....................... 106/161 |
| 4,442,655 A | | 4/1984 | Stroetmann .................. 53/428 |
| 4,515,637 A | | 5/1985 | Cioca ......................... 424/94 |
| 4,563,350 A | | 1/1986 | Nathan et al. ................ 424/95 |
| 4,591,456 A | | 5/1986 | Huc et al. ................... 530/356 |
| 4,760,131 A | | 7/1988 | Sundsmo et al. ........... 530/356 |
| 4,863,732 A | | 9/1989 | Nathan et al. ................ 424/95 |
| 4,880,429 A | | 11/1989 | Stone ......................... 623/18 |
| 4,891,359 A | * | 1/1990 | Saferstein et al. ........... 514/21 |
| 4,894,441 A | | 1/1990 | Menincagli .................. 530/356 |
| 4,953,299 A | | 9/1990 | Gimeno et al. ................ 34/92 |
| 4,963,146 A | | 10/1990 | Li ............................... 606/152 |
| 4,980,403 A | | 12/1990 | Bateman et al. ............. 524/17 |
| 5,028,695 A | * | 7/1991 | Eckmayer et al. .......... 530/356 |
| 5,124,438 A | | 6/1992 | Brueckmann et al. ...... 530/354 |
| 5,219,576 A | | 6/1993 | Chu et al. ................... 424/484 |
| 5,256,418 A | | 10/1993 | Kemp et al. ................. 424/423 |
| 5,274,078 A | | 12/1993 | Wada et al. ................. 530/356 |
| 5,308,889 A | | 5/1994 | Rhee et al. .................. 523/113 |
| 5,331,092 A | | 7/1994 | Huc et al. ................... 530/356 |
| 5,332,475 A | | 7/1994 | Mechanic |
| 5,378,469 A | | 1/1995 | Kemp et al. ................. 424/423 |
| 5,422,264 A | | 6/1995 | Quraranta et al. ........ 530/240.2 |
| 5,562,946 A | | 10/1996 | Fofonoff et al. ........... 427/2.31 |
| 5,639,654 A | | 6/1997 | Bernard et al. ............. 435/325 |
| 5,658,789 A | | 8/1997 | Quaanta et al. ............. 435/375 |
| 5,667,961 A | | 9/1997 | Bernard et al. ................ 435/1 |
| RE35,748 E | | 3/1998 | Luck et al. .................... 514/2 |
| 5,786,421 A | | 7/1998 | Rhee et al. ................. 525/54.1 |
| 5,800,372 A | | 9/1998 | Bell et al. ..................... 602/48 |
| 5,874,537 A | * | 2/1999 | Kelman et al. ............. 530/356 |
| 5,972,366 A | | 10/1999 | Haynes et al. .............. 424/422 |
| 5,997,895 A | * | 12/1999 | Marotam et al. ........... 424/423 |

FOREIGN PATENT DOCUMENTS

| | | |
|---|---|---|
| EP | 0 285 474 | 3/1988 |
| EP | 0 463 887 | 1/1992 |
| EP | 0 463 887 | 12/1995 |
| EP | 0 552 576 | 2/1998 |
| GB | 831124 | 3/1960 |
| JP | 07097715 | 11/1995 |
| WO | WO 93/06791 | 4/1993 |
| WO | WO 95/25482 | 9/1995 |
| WO | WO 95/25550 | 9/1995 |

OTHER PUBLICATIONS

Chvapil M., "Collagen Sponge Theory and Practice of Medical Applications," J. Biomed. Mater. Res., vol. 11:721–741 (1977).

Silverstein ME et al., "Collagen Fibers as a Fleece Hemostatic Agent," J. Trauma, vol. 20: 688–694 (1980).

Silverstein ME et al., "Experimental and Clinical Experiences with Collagen Fleece as a Hemostatic Agent," J. Trauma, vol. 21, No. 5: 388–393 (1981).

Coln D, et al., "Evaluation of Hemostatic Agents in Experimental Splenic Lacerations," Am J. Surg., vol. 145: 256–259 (1983).

Peper, William A et al., "Pigskin as a Topical Hemostat in Arterial, Liver, and Splenic Injuries," *Surgery* vol. 99, No. 5, 1986, pp. 557–563.

Wachol–Drewek, Z et al., "Comparative Investigation of Drug Delivery of Collagen Implants Saturated in Antibiotic Solutions and a Sponge Containing Gentamicin," *Biomaterials,* 1996, vol. 19, No. 17, pp. 1733–1738.

Liening E, et al., "A Comparison of the Biocompatibility of Three Absorbable Hemostatic Agents in the Rat Middle Ear," Otolaryngol Head Neck Surg. (1997) 116:454–457.

Green J., et al., "Application of INSTAT Hemostat in the Control of Gingival Hemorrhage in the Patient with Thrombocytopenia," Oral Surg. Oral Med. Oral Pathol., (1991) 71:27–30.

Wagner W., et al., "Comparitive in Vitro Analysis of Topical Hemostatic Agents," *Journal of Surgical Research,* (1996) 66:100–108.

Johnson & Johnson Product Insert on Web Page for Instat® collagen absorbable hemostat (nine pages).

"Biologically Active Collagen Fibers and Fibrous Materials," *Khim. Volokna,* (1990), vol. 6, pp. 39–41—English Translation provided—(pp. 1–5).

Kato et al., "Formation of Continuous Collagen Fibres: Evaluation of Biocompatibility and Mechanical Properties," *Biomaterials,* (1990) vol. 11, No. 3, pp. 169–175.

Cavallaro et al., "Collagen Fabrics as Biomaterials," *Biotechnology and Bioengineering,* (1994) vol. 43, pp. 781–791.

"Biologically Active Collagen Fibers and Fibrous Materials," *Khim. Volokna,* (1990), vol. 6, pp. 39–41 in Greek—No Translation Provided.

Mancini et al., "A Technique for the Prevention of Automatic Implantable Cardioverter Defibrillator Generator Migration," *Pace* (1990), vol. 13, pp. 946–947.

* cited by examiner

COLLAGEN HEMOSTATIC FOAM

FIELD OF THE INVENTION

This invention relates to the field of hemostatic devices for controlling bleeding.

BACKGROUND OF THE INVENTION

Uncontrolled bleeding can result in shock and death. In surgical patients and patients receiving anticoagulant medication, the problem of rapid blood loss arising from, for example, a hemorrhage of a blood vessel, body tissue, organ or bone can give rise to a life threatening situation.

Biodegradable devices for controlling bleeding are commercially available. However, many of these devices require the impregnation of protein agents such as thrombin or fibrinogen to be effective. Unfortunately, special storage conditions are required to preserve the hemostatic activity of these protein agents. For example, many of these devices must be stored under refrigeration conditions to maintain the bioactivity of the hemostatic devices into which the protein agents have been impregnated. Such requirements prohibit certain field applications of the patch, where refrigeration facilities are unavailable. Another problem with certain commercially available hemostatic devices is their lack of flexibility in the dry state. Many hemostatic devices do not conform easily to the shape of the body surface to which it is applied. In addition, hemostatic devices which further include hemostatic agents, such as thrombin, typically require that the thrombin be reconstituted and added to the dry devices immediately before use to provide a flexible hemostatic device having sufficient hemostatic activity to control bleeding.

SUMMARY OF THE INVENTION

The invention provides a hemostatic device which solves the above-described and other problems of the prior art devices. Methods for preparing the hemostatic devices of the invention also are provided. The hemostatic devices of the invention do not require exogenously added protein agents to be effective. Accordingly, the hemostatic devices of the invention can withstand elevated temperatures and do not require refrigeration to retain hemostatic efficacy. In addition, the hemostatic devices disclosed herein are easy to use and mold easily to body contours. Accordingly, the hemostatic devices of the invention are particularly useful for treating the problematic hemorrhages of parenchymal organs, spine, and brain. Such hemostatic devices can be sterilized and packaged in a sterile package for pharmaceutical applications.

According to one aspect of the invention, a process for preparing a hemostatic device of the invention is provided. The process involves: (a) suspending a plurality of collagen particles in water to form a collagen slurry, wherein the collagen particles have a bulk density sufficient to form a suspension in water and wherein the collagen slurry has a concentration in the range of about 1% to about 2% (weight/volume); and (b) lyophilizing (freeze-drying) the collagen slurry to form a hemostatic device. The hemostatic devices that are formed in accordance with this method are foams, preferably reticulated open cell foams. Foams also are referred to in the art as "sponges". Preferably, the collagen particles of the hemostatic device have a hemostatic activity that is equivalent to the hemostatic activity of the collagen particles from which the hemostatic device is formed. More preferably, the hemostatic devices are formed of Avitene® flour and the collagen particles of the hemostatic devices of the invention have a hemostatic activity equivalent to the hemostatic activity of Avitene® flour.

Hemostasis is a term of art which refers to cessation of bleeding. Although not wishing to be bound to any particular theory or mechanism, it is believed that avoiding contact between the collagen particles and an acid solution and minimizing exposure of the collagen to denaturing conditions, such as excessive mechanical shear, high temperature, or long $H_2O$ residence times, during the fabrication process results in a greater retention of hemostatic activity by the collagen particles compared to particles which are subjected to such denaturing conditions. Accordingly, the hemostatic devices of the invention have a greater hemostatic activity compared to conventional collagen hemostatic devices in which the fabrication process has involved dissolution of collagen in acid solution.

In one embodiment of the invention, the method for forming a hemostatic device of the invention involves suspending a plurality of collagen particles (preferably, collagen fibrils) in water to form a collagen slurry and subjecting the collagen slurry to lyophilization (freeze-drying) to form the hemostatic device. The collagen particles have a bulk density sufficient to form a suspension in water. In general, the bulk density of the collagen particles is in the range of about 1.5 to about 3.5 lbs/ft$^3$ and, more preferably, from about 2 to about 3 lbs/ft$^3$. The particles are suspended in water to obtain a collagen concentration in the range of about 1% to about 2% (weight/volume), and, more preferably, in the range of about 1.1% to about 1.64% (weight/volume). In the preferred embodiments, the hemostatic devices are formed of collagen particles that have not been subjected to acid dissolution or other denaturing conditions.

According to yet another aspect of the invention, a product prepared by the above-described process is provided. A particular embodiment of this process in provided in the Examples. The process, optionally, further includes the step of cross linking the collagen within the hemostatic devices of the invention, e.g., by heating the collagen fibers of the invention at a temperature and for a period of time sufficient to form crosslinks, preferably, without substantially reducing the hemostatic activity of the collagen fiber. Preferably, the crosslinked hemostatic devices retain at least about 80%, more preferably, at least about 90% and, most preferably, at least about 95% hemostatic activity compared to the hemostatic activity of the hemostatic device prior to crosslinking.

In certain preferred embodiments, the hemostatic device is formed of collagen particles that have a hemostatic activity equivalent to the hemostatic activity of the collagen particles from which the device is formed. In the preferred embodiments, the hemostatic device is formed of collagen flour, preferably Avitene® flour, that has not been subjected to acid dissolution. In these and other embodiments, the hemostatic device preferably has a density of from about 0.015 to about 0.023 gm/cc; and/or a weight percent solids ranging from about 1.10 to about 1.64 weight percent.

In yet other embodiments, the hemostatic device of the invention is formed of collagen and has a hemostatic activity in a pig spleen animal model of hemostasis that corresponds to one tamponade for a hemostatic device having a thickness of ⅜ inch, a length of ½ inch, and a width of ½ inch. An exemplary pig spleen animal model of hemostasis is provided in the Examples.

In certain embodiments, the hemostatic devices of the invention further include a hemostasis-promoting amount of at least one hemostatic agent. As used herein, a "hemostasis-promoting amount" is the amount effective to accelerate clot formation at an interface between a surface (e.g., of a wound or lesion) and the hemostatic device. Exemplary hemostatic agents include a thrombin molecule, a fibrinogen molecule, a source of calcium ions, an RGD peptide, protamine sulfate, an epsilon amino caproic acid, and chitin. In the preferred embodiments, the hemostatic agent is thrombin. The hemostatic agents can be introduced into the hemostatic devices at any stage during the preparation of these devices, including adding the hemostatic agent to the collagen slurry, lyophilizing the agents into the hemostatic device during its preparation or applying the agents to the device post-processing.

In certain embodiments, the hemostatic devices of the invention further include a therapeutically effective amount of at least one therapeutic agent, such as agents which promote wound-healing and or reduce pain (e.g., vascular pain). Agents which promote wound-healing and/or reduce pain include anti-inflammatory agents (steroidal and non-steroidal) such as agents which inhibit leukocyte migration into the area of surgical injury, anti-histamines; agents which inhibit free radical formation; and bacteriostatic or bacteriocidal agents.

Various additives, optionally, can be incorporated into the hemostatic devices of the invention without substantially reducing the hemostatic activity of these devices. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the collagen fibrils of the present invention, and with each other, in a manner such that there is no interaction which would substantially impair the desired hemostatic activity.

The hemostatic devices of the invention preferably have one or more mechanical (e.g., tensile strength, wettability) and/or functional (hemostatic activity) properties that are equivalent to or greater than those of commercially available hemostatic devices, such as Gelfoam® 100 (Upjohn Company), Actifoam® (Davol Inc., Cranston, R.I.) and Helistat® (Johnson & Johnson Medical Inc., Arlington, Tex.). Gelfoam® is an absorbable gelatin sponge and is described in U.S. Pat. No. 2,465,357. Actifoam® is a crosslinked collagen sponge and is described in U.S. Pat. Nos. 4,953,299 and 5,331,092. Helistat® is an absorbable collagen sponge that is formed of tendon collagen.

The hemostatic devices of the invention can be formed into a variety of shapes. In certain embodiments, the hemostatic device is in the form of a flexible sheet which, optionally, is packaged in a sterile package. More complex shapes also are contemplated.

The hemostatic devices of the invention are useful for promoting hemostasis at a site of bleeding (e.g., reducing or eliminating bleeding from a wound). Accordingly, a further aspect of the invention involves methods for promoting hemostasis. In general, such methods of the invention involve manually pressing a hemostatic device of the invention against a bleeding surface, such as a surface of a wound or a surface of a lesion on an organ, tissue or other bleeding surface of, e.g., a parenchymal organ (e.g., spleen, liver, lung or pancreas), a spine, a brain, for a period of time until clotting has occurred at the interface between the hemostatic device and the surface.

A number of embodiments of the invention are summarized above. However, it should be understood that the various limitations presented in each embodiment are not mutually exclusive and, accordingly, the limitations can be combined to obtain further aspects of the invention.

DETAILED DESCRIPTION OF THE PREFERRED EMBODIMENTS

Figure 1:
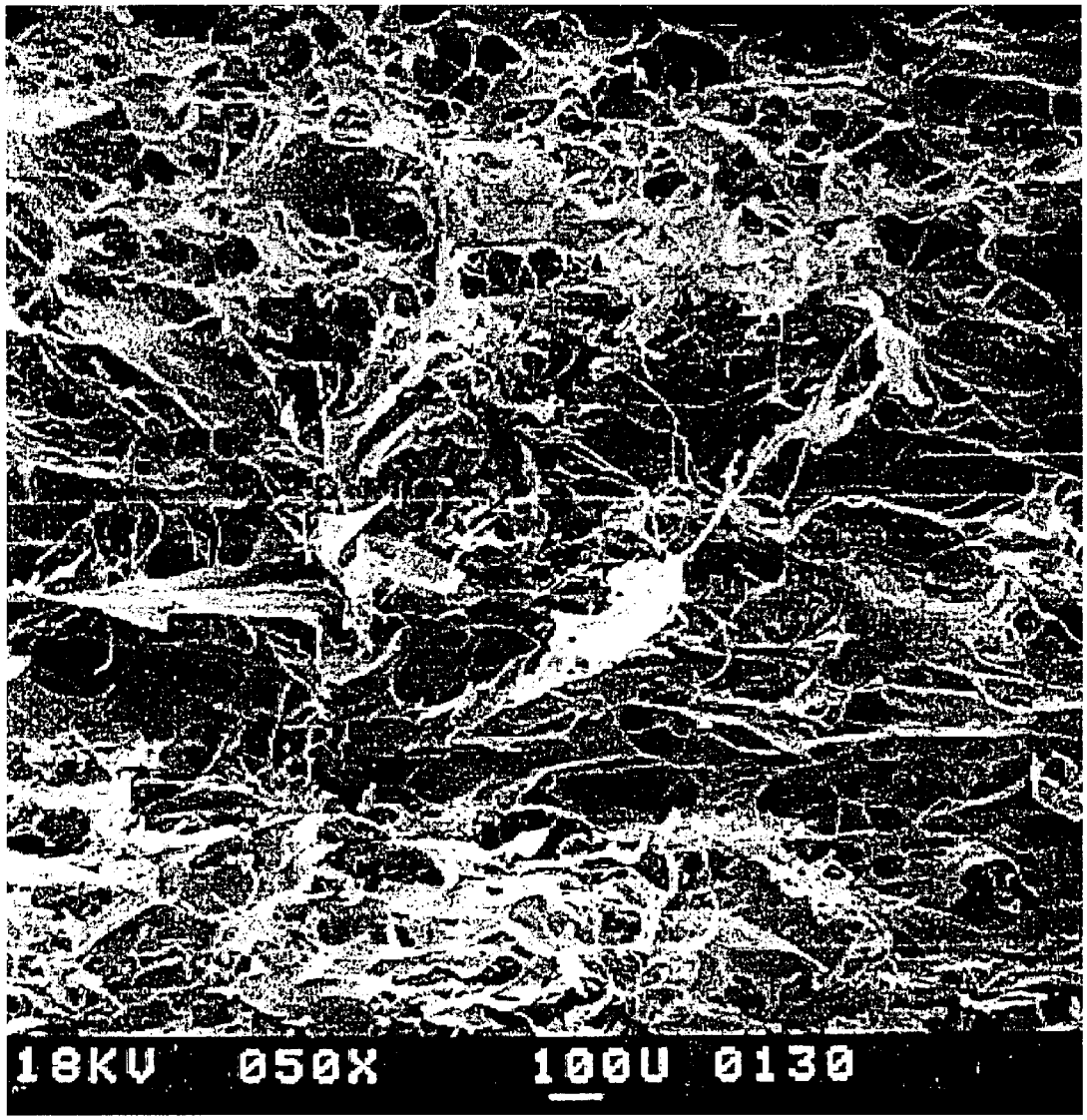
FIG. 1 shows a reticulated open cell foam structure as illustrated in the SEM image for a representative hemostatic device of the invention.

According to one aspect of the invention, a device having hemostatic activity ("hemostatic device") is provided. The hemostatic device comprises a shaped structural element that is a biodegradable matrix formed of a collagen, such as a microfibrillar collagen (e.g., absorbable Avitene® flour), which has not been subjected to acid dissolution and which has been exposed to minimal denaturing conditions. Although applicants do not wish to be bound to one particular theory or mechanism, it is believe that avoiding contact of the collagen with acid solution and minimizing exposure of the collagen to denaturing conditions prior to and during the process for forming the device, results in a greater retention of the hemostatic activity by the collagen starting material. In a preferred embodiment, the hemostatic device of the invention is formed of collagen flour, preferably Avitene® flour, which has not been subjected to acid dissolution or exposed to denaturing conditions, such as, e.g., excess mechanical shear, high temperatures or long water residence times. Accordingly, the invention provides hemostatic devices having unexpected improved hemostatic properties compared to the hemostatic devices of the prior art that are formed by processes which involve collagen dissolution in acid solution or exposure to denaturing conditions.

According to one aspect of the invention, a method for preparing a hemostatic device is provided. The method involves: (a) suspending a plurality of collagen particles (preferably, collagen fibrils) in water to form a "collagen slurry", wherein the collagen particles have a bulk density sufficient to form a suspension in water (preferably, in the range of about 1.5 to about 3.5 lbs/ft$^3$) and wherein the collagen slurry has a collagen concentration in the range of about 1% to about 2% (weight/volume); and (b) lyophilizing the collagen slurry to form a hemostatic device. In certain preferred embodiments, the collagen particles that are used to form the hemostatic devices of the invention have a bulk density in the range of about 2 to about 3 lbs/ft$^3$. In these and other preferred embodiments, the collagen slurry has a collagen concentration in the range of about 1.1% to about 1.64% (weight/volume).

The process of the invention avoids dissolving the collagen in acid solution and minimizes exposure of the collagen to other process steps which could denature the collagen and, thereby, adversely affect its hemostatic activity. In the preferred embodiments, the collagen is microfibrillar collagen; more preferably, a collagen flour such as Avitene® flour. Accordingly, in certain embodiments, the collagen particles of the hemostatic devices of the invention have a hemostatic activity that is about the same hemostatic activity as Avitene® flour. Avitene® flour is a microfibrillar collagen hemostat that is indicated for all surgical specialties, including neurosurgery, vascular, orthopaedic, urologic, and other general procedures. Avitene® is available from Davol, Inc. (product numbers 101001, 101002, 101003, 101004, and 101034, Cranston, R.I.). The process for preparing Avitene® flour is described in U.S. Pat. No. 3,742,955, issued to Battista et al.

As used herein, "hemostatic activity" refers to the ability to stop bleeding and can be determined, e.g., in animal models that are recognized as predictive of an in vivo effect by those of ordinary skill in the art. Exemplary hemostasis animal models include the pig and dog spleen animal models. A preferred animal model for assessing hemostasis activity is provided in the Examples.

Optionally, the method for preparing the hemostatic devices of the invention further includes the step of introducing the collagen slurry into a mold prior to the lyophilizing the collagen slurry. The mold is of sufficient dimension to contain the slurry during the lyophilization step and to provide a template for establishing the final dimensions of the hemostatic device. In the preferred embodiments, the process also includes the step of removing a surface layer of the hemostatic device ("skiving") to remove the thin skin which forms on the surface of the hemostatic device during lyophilization.

Optionally, the method for preparing the hemostatic devices of the invention further includes the step of crosslinking the hemostatic device to form a crosslinked hemostatic device. Crosslinking can be accomplished in various ways and the extent of crosslinking can be assessed in assays which measure, e.g., the wettability of the device or its tensile strength. Representative assays for measuring these parameters are provided in the Examples. Exemplary procedures for crosslinking the hemostatic devices of the invention include: (1) contacting the collagen slurry with 1-ethyl-3-(3-dimethylaminopropyl carbodiimide HCl (EDC) for a period of time and under conditions sufficient to form a crosslinked-hemostatic device; (2) heating the lyophilized hemostatic device for a period of time and under conditions sufficient to form a crosslinked-hemostatic device; (3) exposing the lyophilized hemostatic device to an electron beam for a period of time and under conditions sufficient to form a crosslinked-hemostatic device; and (4) exposing the lyophilized hemostatic device to gamma sterilization for a period of time and under conditions sufficient to form a crosslinked-hemostatic device.

According to another aspect of the invention, the processes for forming the hemostatic devices of the invention further include the step of introducing a hemostatic agent into the hemostatic device. The hemostatic agent can be introduced into the hemostatic device of the invention at any stage in the process, including before the device-formation step (e.g., by adding the hemostatic agent to the slurry) and after device formation step (e.g., by soaking the hemostatic device in a solution containing one or more hemostatic agents).

It is believed that the hemostatic devices of the invention do not require a hemostatic agent to function effectively to control bleeding, e.g., hemorrhage of a parenchymal organ. As a result, the hemostatic devices of the invention which do not further contain a hemostatic agent have good thermal stability and can be stored for months to a few years without refrigeration and loss of effectiveness. Such embodiments of the invention are useful for various medical situations and are particularly useful for field and emergency use, since each may be stored in a ready-to-use state for a lengthy period, even in the absence of refrigeration. Such devices of the invention also are less expensive to make and/or use compared to hemostatic devices which contain a further hemostatic agent to achieve a comparable level of hemostatic activity.

One advantage of the hemostatic devices of the invention is their flexibility compared to hemostatic devices such as Gelfoam®, that is, the hemostatic devices of the invention can be provided in a form that easily conforms to the contours of an organ or biological surface, making the manipulation of applying the devices quicker to perform. As a result, there is less overall blood loss to the patient and less time is spent in surgery. Further, the hemostatic devices of the invention can be applied, in wet or dry state, to a bleeding site and do not require wetting with a sterile solution prior to use or to conform to the contour of the biological surface to which it is applied.

The hemostatic devices of the invention preferably are formed of an absorbable collagen from any source, e.g., corium collagen, tendon collagen, and, more preferably, the devices are formed of a microfibrillar collagen, including a collagen flour, such as Avitene® flour. The effectiveness of devices of the present invention in promoting clot formation is further enhanced by their lattice structures which are of a sufficient size to promote enzyme substrate interactions. In particular, the structure of the hemostatic devices of the invention are selected to enhance contact between thrombin that, optionally, is provided exogenously in the devices with endogenous fibrinogen present in the blood exuding from a wound or lesion of, e.g., a parenchymal organ, a spine or a brain.

In certain embodiments, at least one hemostatic agent can be included in the hemostatic devices of the invention. Because certain combinations of hemostatic agents can act synergistically, the amount of each hemostatic agent can be less than that which would be required to improve the hemostatic activity of the hemostatic devices of the invention if the agents were used individually. Accordingly, the collective amount of the hemostatic agent(s) which are included in the hemostatic devices of the invention is a "hemostasis-promoting amount", i.e., the amount of at least one hemostatic agent effective to accelerate clot formation at an interface between a surface (e.g., of a wound, of a lesion on a parenchymal organ, the spine or the brain) and a hemostatic device of the invention.

Exemplary hemostatic agents that can be applied to the hemostatic devices of the invention in amounts effective for stimulating hemostasis, include, but are not limited to: thrombin, an enzyme which converts fibrinogen to fibrin; calcium, sodium, magnesium or other ions that stimulate hemostasis; protamine sulfate, an epsilon amino caproic acid, fibrinogen, and chitin. Epsilon amino caproic acid and its analogs which possess a similar chemical structure and hemostatic activity for use in a hemostatic device are described in U.S. Pat. No. 5,645,849, assigned to Clarion Pharmaceuticals. In terms of ion additives, calcium chloride is generally a preferred additive for introducing a calcium ion into the device.

Additionally or alternatively, the tripeptide RGD, composed of arginine, glycine and aspartic acid, and optionally serine "RGDS," can be incorporated into the hemostatic devices of the invention as a hemostatic agent. RGD is the active site of fibrinogen and fibronectin. RGD accelerates wound healing and is believed to stimulate fibroblast migration. The RGD additive is also much less expensive than fibrinogen because it can be synthesized using solid phase chemistry.

Protamine sulfate can be added to the hemostatic devices of the invention in an amount that is effective to neutralize heparin in the local environment of the device. In general, the amount of protamine sulfate is an amount between about 1–15 mg/cm$^2$ of the hemostatic device, more preferably, an amount between 2–5 mg/cm$^2$ of a wound contacting surface of the hemostatic device.

Likewise, RGD or RGDS peptide can be dissolved in double distilled water and sprayed onto a wound-contacting surface of a hemostatic device of the invention. Preferably, such embodiments of the invention contain an amount of RGD effective to enhance clot formation. For example, RGD or RGDS can be applied to a hemostatic device of the invention in an amount between about 110–130 mg/cm$^2$. Thus, a standard size hemostatic device that is a fabric would contain about 1–10 mg/fabric or about 5–7 mg/fabric of RGD or RGDS.

Thrombin is an active ingredient found in other hemostatic devices. It is believed that the collagen particles of the hemostatic devices of the invention have a hemostatic activity that is equivalent to the hemostatic activity of the collagen particles from which the device is formed. Thus, the invention (without thrombin) advantageously provides a device having enhanced hemostatic activity compared to the hemostatic devices of the prior art. A further increase in the hemostatic activity of the hemostatic devices of the invention can be achieved by, optionally, including a hemostatic agent in the hemostatic devices.

As used herein, the term "equivalent" with respect to hemostatic activity means that the hemostatic activity is substantially the same when measured in the same activity assay. An exemplary hemostatic activity assay, a pig spleen hemostasis assay, is provided in the examples. The assay can be used to measure the hemostatic activity of the devices of the invention and can also be used to measure the hemostatic activity of the collagen particles, e.g., collagen flour, from which the hemostatic device is formed by, for example, by placing powder over the incision, overlaying the powder with a sterile gauze, and applying pressure to the wound in the same manner as described in the example for a device of the invention. The experimental results for the pig spleen assay are reported in terms of the number of tamponades necessary to achieve hemostasis at an incision in the pig spleen. The number of tamponades for multiple samples is determined to obtain a distribution of the number of tamponades. The distribution of tamponades is a measure of the hemostatic activity for the device or flour that is being tested. Accordingly, devices which have a similar distribution of tamponades have "equivalent" hemostatic activity. For example, if 80 of 100 samples of a first device require one tamponade to achieve hemostasis, and 70 of 100 samples of a second device require one tamponade to achieve hemostasis, the hemostatic activity of the second device is considered to be within 10% of the hemostatic activity of the first device. Equivalent hemostatic activity means that the hemostatic activity for two samples are within at least 50%, more preferably, within 60%, 70%, 80%, 90% and, most preferably, within 95%.

The preferred hemostatic agent is thrombin (e.g., human or bovine thrombin). Preferably, the thrombin is a recombinant thrombin to avoid viral or other contamination from the organism from which the thrombin is derived. The molecules "thrombin" and "fibrinogen", as defined herein, are meant to include natural thrombin and fibrinogen molecules derived from an animal or human origin, a synthetic form or a recombinant form of the molecules, including functionally active analogs that effectively maintain the enzyme's clot promoting activity in an animal or human. The species of animal from which the molecule is derived can vary and depends on the intended use of the hemostatic device. For example, a hemostatic device intended for human use for safety reasons preferably contains recombinant human thrombin or non-human thrombin, e.g, bovine thrombin. By avoiding use of human fibrinogen isolated from a human tissue or using viral deactivated human thrombin, risks associated with viral contamination of purified blood products are minimized.

Thrombin and/or other hemostatic agents or additives described as components of a hemostatic device according to the invention, can be applied to the hemostatic device by any of several methods which, preferably, are performed under sterile conditions. Thrombin can be applied as a layer to a particular surface or side of a hemostatic device of the invention, which surface is then designated the wound-contacting surface. For example, this can be accomplished by spraying thrombin in powder form onto a hemostatic device of the invention. Alternatively, a solution of thrombin can be coated onto a hemostatic device of the invention and dried by lyophilization or by conventional means. In another method of applying thrombin, a hemostatic device of the invention is dipped completely or partially into a sterile solution of thrombin such that a sufficient amount of thrombin accumulates within the hemostatic device effective to inhibit fibrinolysis in a mammal. Preferably, the thrombin solution contains 1000 I/U of thrombin dissolved in 1 ml saline. The amount of thrombin applied in the solution can vary. Preferably, the total amount of thrombin applied to a hemostatic device of the invention or surface thereof is 100–1000 units/cm$^3$. It is understood that alternative methods of applying the hemostatic agents and additives to a hemostatic device of the invention in addition to the methods described herein also can be used.

The hemostatic devices of the invention that have been soaked in thrombin solution or other solution containing a hemostatic agent optionally can be dried. The drying step can be accomplished by lyophilization. Other drying procedures appropriate for a material containing an active protein ingredient can also be employed, so long as the drying procedure does not denature the proteins or render them inactive. Alternatively, hemostatic device can be dried by maintaining it at room temperature for a period of 1–3 hours, followed by refrigeration overnight.

In certain embodiments, the hemostatic devices of the invention further include a therapeutically effective amount of one or more therapeutic agents, such as an agent which promotes wound-healing. Agents which promote wound-healing include anti-inflammatory agents such as agents which inhibit leukocyte migration into the area of surgical injury, anti-histamines; agents which inhibit free radical formation; and bacteriostatic or bacteriocidal agents. In general, a therapeutically effective amount means that amount necessary to delay the onset of, inhibit the progression of, or halt altogether the particular condition being treated. Generally, a therapeutically effective amount will vary with the subject's age, condition, and sex, as well as the nature and extent of the condition in the subject, all of which can be determined by one of ordinary skill in the art. The dosage of therapeutic agent contained in the hemostatic devices of the invention may be adjusted to accommodate the particular subject and condition being treated.

As used herein, the phrase, "agents which promote wound-healing" refers to agents, the administration of which, promote the natural healing process of a wound. Agents that promote wound-healing include anti-inflammatory agents, agents which inhibit free radical formation, and bacteriostatic or bacteriocidal agents.

Anti-inflammatory agents are agents which inhibit or prevent an immune response in vivo and include: (i) agents which inhibit leukocyte migration into the area of surgical injury ("leukocyte migration preventing agents"), and anti-histamines. Representative leukocyte migration preventing agents include silver sulfadiazine, acetylsalicylic acid, indomethacin, and Nafazatrom. Representative anti-histamines include pyrilamine, chlorpheniramine, tetrahydrozoline, antazoline, and other anti-inflammatories such as cortisone, hydrocortisone, beta-methasone, dexamethasone, fluocortolone, prednisolone, triamcinolone, indomethacin, sulindac, its salts and its corresponding sulfide, and the like.

Representative agents which inhibit free radical formation include antioxidants that inhibit the formation and/or action of oxide products, superoxide dismutase (SOD), catalase, glutathione peroxidase, b-carotene, ascorbic acid, transferrin, ferritin, ceruloplasmin, and desferrioxamine α-tocophenol.

Representative bacteriostatic or bacteriocidal agents include antibacterial substances such as β-lactam antibiotics, such as cefoxitin, n-formamidoyl thienamycin and other thienamycin derivatives, tetracyclines, chloramphenicol, neomycin, gramicidin, bacitracin, sulfonamides; aminoglycoside antibiotics such as gentamycin, kanamycin, amikacin, sisomicin and tobramycin; nalidixic acids and analogs such as norfloxican and the antimicrobial combination of fluoroalanine/pentizidone; nitrofurazones, and the like.

The hemostatic devices of the invention can contain one or more therapeutic agents, alone or in combination with one or more hemostatic agents.

Various additives, optionally, can be incorporated into the hemostatic devices of the invention without substantially reducing the hemostatic activity of these devices. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the collagen particles (e.g., fibrils) of the present invention, and with each other, in a manner such that there is no interaction which would substantially impair the desired hemostatic activity.

According to yet another aspect of the invention, a product prepared by the above-described process is provided. A particular embodiment of this process in provided in the Examples.

According to yet another aspect of the invention, a hemostatic device is provided which has a hemostatic activity in a pig spleen animal model of hemostasis that corresponds to one tamponade for a hemostatic device having a thickness of ⅜ inch, a length of ½ inch, and a width of ½ inch. A detailed description of the pig spleen animal model is provided in the Examples.

The hemostatic devices of the invention can be used in a wet or in a dry state. Preferably, the hemostatic devices of the invention have a wettability index that is equivalent to or less than that of Gelfoam® (without Thrombin). As used herein, a "wettability index" refers to the time it takes for a sample of known dimension to fully hydrate. A preferred embodiment of the invention which are illustrated in the Examples has a wettability index of less than or equal to 1 minute in distilled water at room temperature.

Preferably, the hemostatic devices of the invention, when wet or dry, have a hemostatic response time that is equivalent to or less than that of Gelfoam® (with or without Thrombin). Gelfoam® refers to a collagen hemostat formed of denatured collagen that is available from the Upjohn Company, (product number 0342-01, 0315-01, 0353-01, 0315-02, 0349-01, 0301-01, 0323-01, 0433-01, Kalamazoo, Mich. 49001).

In certain embodiments, the hemostatic device of the invention has a higher percentage of solids than typically is found in hemostatic devices of the prior art. It is believed that the higher percentage of solids increases the mechanical strength properties of the hemostatic device. Preferably, the hemostatic devices of the invention have a density in the range of about 0.01 to about 0.030 gm/cc, more preferably, a range of about 0.015 to about 0.023 gm/cc; and a weight percent solids ranging from about 1.0–2.0 in the slurry prior to lyophilization, more preferably, in the range of about 1.10 to about 1.64 weight percent. In general, the hemostatic devices of the invention have a melting point (Tm) in the range of about 93.4 to about 105.7° C., as determined by differential scanning calorimetry, depending upon the moisture content of the device.

Representative embodiments which satisfy some or all of the foregoing criteria, when wet, have an acute mechanical strength and a chronic mechanical strength that are equivalent to or greater than that of Gelfoam® 100. Gelfoam® 100 refers to a collagen hemostat that is available from the Upjohn Company (product number 0342-01, 0315-01, 0353, 01, 0315-02, 0349-01, 0301-01, 0323-01,0433-01, Kalamazoo, Mich. 49001). As used herein, an "acute mechanical strength" refers to immediate tensile testing after full wetting and is determined by tensile testing, according to a standard procedure such as illustrated in the Examples. Mechanical strength is, in part, a function of the state of the hemostatic device (wet versus dry), as well as a function of its dimensions. For embodiments in which the hemostatic device has a thickness of about ⅜ inch to about ½ inch width, the acute maximum load for the device, when wet, is $\geq 0.08$ lbs (minimum) with the mean acute maximum load being about 0.14 lbs.

In certain embodiments of the invention, the hemostatic device, when dry, has a modulus equivalent to or greater than that of Actifoam®. Actifoam® refers to a collagen hemostat that is available from Davol, Inc. (Cranston, R.I.). The process for preparing Actifoam® is described in U.S. Pat. Nos. 4,953,299 and 5,331,092. As used herein, "modulus" refers to stiffness and is determined by tensile testing in accordance with standard procedures such as those described in the Examples. In certain embodiments, the modulus for the hemostatic device, when dry, is less than or equal to 86 psi.

Advantageously, the hemostatic devices of the invention need not contain a hemostatic agent to function effectively to control bleeding, e.g., hemorrhage of a parenchymal organ. As a result, the hemostatic devices of the invention which do not further contain a hemostatic agent have good thermal stability and can be stored for months to a few years without refrigeration and losing effectiveness. Such embodiments of the invention are useful in various situations, including field and emergency use, since each may be stored in a ready-to-use state for a lengthy period.

One advantage of the present invention is its flexibility compared to hemostatic devices such as Gelfoam® (which is rigid when dry), that is, the hemostatic devices of the invention can be provided in a form that easily conforms to the contours of an organ or biological surface, making the manipulation of applying the device quicker to perform. As a result, there is less overall blood loss to the patient and less time is spent in surgery. A further advantage of using the hemostatic devices of the invention in a dry state is that the dry devices can absorb blood exuding from a biological surface, thereby further promoting hemostasis at the interface of the hemostatic device and the biological surface.

The hemostatic devices of the invention preferably are formed of an absorbable collagen (e.g., microfibrillar collagen) as a matrix. In the preferred embodiments, the matrix is a flat layer of microfibrillar collagen foam that is formed of Avitene® flour. The effectiveness of devices of the present invention in promoting clot formation is enhanced by their lattice structures, which promote enzyme substrate interactions. In particular, the collagen foam structure enhances contact between thrombin that optionally is provided exogenously in the device with endogenous fibrinogen present in the blood exuding from a wound or lesion of a parenchymal organ. A representative hemostatic device prepared according to the process disclosed herein has a reticulated open cell foam structure as illustrated in the SEM image (FIG. 1).

According to certain embodiments, a hemostatic device of the invention is contained within a sealed sterile package which facilitates removal of the device without contamination. Such a package, for example, can be an aluminum foil pouch or other material that is easily sterilized. Radiation, e.g., gamma radiation, can be applied to sterilize the device and packaging material together. In yet other embodiments, a container having dual compartments is provided in which a first compartment contains distilled water, sterile saline or a sterile buffer, and a second compartment contains a hemostatic device of the invention. In field use, the device of the second compartment can be readily dipped into an opened first compartment and subsequently applied to the wound.

According to still another aspect of the invention, a method for promoting hemostasis is provided. The method involves the steps of pressing a hemostatic device of the invention against a surface of a wound or a surface of a lesion on an organ, tissue, or other biological surface, e.g., a parenchymal organ, the spine or the brain, for a period of time until clotting has occurred at the interface between the hemostatic device of the invention and the surface. The device may be applied to the surface in a dry state or, alternatively, may be soaked in sterile saline solution or a sterile hemostatic agent-containing solution prior to use. Use of a hemostatic device of the invention according to the invention, without first soaking in saline solution permits quick and simple application of the device in various situations, including field situations such as may be encountered by an emergency medical technician. In certain embodiments, the hemostatic device is soaked in a thrombin solution prior to use to introduce a therapeutically effective amount of thrombin into the device. Thus, a hemostatic device of the invention of the invention can be used by applying a "wound-contacting" surface of the device, a surface intended to contact the wound and containing hemostatic agent(s) and, optionally, additives, with or without prior soaking in a sterile solution, to a surface of a bleeding wound or lesion. Then, the device is maintained in contact with the surface for a period of time sufficient for clotting to occur at the interface between the hemostatic device of the invention and the surface and for bleeding to be substantially arrested. In general, the device is maintained in contact with the surface for a period of about 3–20 minutes, preferably, 3–10 minutes, and more preferably, 3–5 minutes.

Where thrombin and/or other hemostatic agents also are present on/in the hemostatic device, the time period preferably is about 5 minutes. The hemostatic device is held in place against the biological surface, preferably with light pressure, e.g., by means of a sterile saline soaked sponge. Alternatively, the hemostatic fabric may be held in place simply by applying pressure to the hemostatic device by means of a gauze or other dry sterile material. Depending on the location of the wound, a bandage can be wrapped around the hemostatic device to provide light pressure on the wound surface.

The efficacy of the hemostatic devices of the invention can be assessed in art-recognized animal models that are believed to be predictive of an in vivo hemostatic effect in humans. For example, surgical lesions induced in parenchymal organs of pigs provide a good model system for hemostasis in the analogous human organs as evidenced by preclinical studies which employ pig models. See e.g., SWINE AS MODELS IN BIOMEDICAL RESEARCH, Swindle, M., Iowa State Univ. Press (1992).

A preferred use of a hemostatic device according to the present invention is to inhibit or completely stop bleeding of a parenchymal organ, such as the liver, kidney, spleen, pancreas or lungs. Other preferred uses are to inhibit or completely stop bleeding of a wound or lesion on the spine or brain. Additional uses for the hemostatic devices of the invention include inhibiting bleeding during surgery, e.g., internal/abdominal, vascular (particularly for anastomosis), urological, gynecological, thyroidal, neurological, tissue transplant uses, dental, cardiovascular, cardiothoracic, ENT (ear, nose, throat) and orthopedic surgeries.

Another use of a hemostatic devices of the invention is topical treatment, such as for burn or tissue transplants and as dura replacement or substitutes. A hemostatic device of the invention for topical use preferably contains additives, such as anti-infection medicaments, bactericides, fungicides and wound healing agents, for example, neomycin and bacitracin.

In addition to inducing hemostasis, the hemostatic devices of the inventions of the invention can be used to hermetically seal body tissue. For example, when air leaks from a wound in the lungs, a hemostatic device of the invention can be applied to the surface surrounding the wound, held in place for a period of time sufficient to induce hemostasis and allow a hermetic seal to form.

The hemostatic devices of the invention also are useful for treating animals, preferably humans or other mammals, including domestic mammals and livestock.

The hemostatic devices of the invention can be provided in a variety of sizes and shapes, depending upon its intended use. Typically, the hemostatic devices of the invention are provided in a standard size rectangular foam, e.g., 8 cm×12.5 cm×1 cm; 8 cm×12.5 cm×3 mm; 8 cm×6.25 cm×1 cm; 8 cm×25 cm×1 cm; 2 cm×6 cm×7 mm; 2.5 cm×2.5 cm×7 mm; with an outer dimensional tolerance of ±⅛ inch and a thickness tolerance of ±1/16 inch. The hemostatic devices may be cut to size with a pair of scissors. The hemostatic devices of the invention may be spherically, conically, cuboidally or cylindrically-shaped or prefabricated into small squares, such as for packing into a body cavity, such as a dental cavity following a tooth extraction. Alternatively, the hemostatic device can be shaped for epistaxis (profusely bleeding nostril) or insertion into a cavity. The hemostatic devices of the invention that are intended for topical applications can be applied with an adhesive tape, as a band-aid form, where the hemostatic device is adhered to an adhesive backing. One or more additional layers of wound dressing material, preferably a layer which aids in absorption of blood or other exudants, can be applied to or incorporated into the hemostatic devices of the invention to form a stronger bandage. Alternatively, the layer may be applied as a supplement to the backside (non-wound contacting surface) of a device according to the invention. Particularly for topical use, the layer(s) can contain superabsorbents to wick exudant solution from the wound site. For hemostatic devices of the inventions intended for internal-surgical applications, where an added layer(s) is integral with the device, the layer(s) should be both biodegradable and pharmaceutically acceptable.

The hemostatic devices of the invention can be designed to facilitate its application to fuse ends of a blood vessel or other body lumen having been severed, e.g., surgically. To apply a hemostatic device for anastomosis, a rectangular fabric, for example, is wrapped around the external surface of the ends of a Dacron® graft and the graft is positioned into place. The hemostatic device portion of the graft accelerates fibrin growth into the graft to seal the graft in place (hemostatically and hermetically). According to certain embodiments of the invention, a kit is provided for this application. The kit contains a graft and a hemostatic device of the invention that is designed for fitting with the ends of the graft. Alternatively, a kit is provided having a hemostatic device of the invention pre-fitted onto at least one end of a graft.

According to still other aspects of the invention, various specialized kits can be provided. The kits contain any of the hemostatic device embodiments disclosed herein and a package, wherein the hemostatic device of the invention is contained within a sealed sterile package which facilitates removal of the fabric without contamination. The kit can contain multiple hemostatic devices of the inventions, preferably wherein each hemostatic device is contained within a separate sealed sterile package. A kit that is designed for autonomous use, e.g., for field/military use can, in addition to a hemostatic device of the invention, further include disposable pre-sterilized surgical instruments and/or agents that can be incorporated into the device, e.g., thrombin, calcium chloride.

Unless defined otherwise, all technical and scientific terms used herein have the same meaning as commonly understood by one of ordinary skill in the art of the invention. Although any methods and materials similar or equivalent to those described herein can be used in the practice of the invention, the preferred methods and materials have been described. Unless mentioned otherwise, the techniques employed or contemplated herein are standard methodologies well known to one of ordinary skill in the art. The materials, methods and examples are illustrative only and not limiting.

EXAMPLES

Example 1

Preparation of a Preferred Embodiment

Description of Ultrafoam™

Ultrafoam™ is an absorbable hemostatic sponge prepared as a sterile, porous, pliable, water insoluble partial hydrochloric acid salt of purified bovine corium collagen. Ultrafoam™ consists of lyophilized Avitene® flour and water. In its manufacture, swelling of the native collagen fibrils is controlled by ethyl alcohol to permit noncovalent attachment of hydrochloric acid to amine groups on the collagen molecule and preservation of the essential morphology of native collagen molecules. The characteristics of collagen which are essential to its effect on the blood coagulation mechanisms are substantially preserved, although dry heat sterilization causes some cross linking which is evidenced by reduction of hydrating properties, and a decrease of molecular weight which implies some limited amount of degradation of collagen molecules.

Ultrafoam™ sizes are:

| | |
|---|---|
| 1 cm × 1 cm × 7 mm | 2.5" × 2.5" × ¼" |
| 2 cm × 6 cm × 7 mm | ¾" × 2.5" × ¼" |
| 8 cm × 6.25 cm × 1 cm | 3⅛" × 2.5" × ⅜" |
| 8 cm × 12.5 cm × 1 cm | 3⅛" × 5" × ⅜" |
| 8 cm × 25 cm × 1 cm | 3⅛" × 10" × ⅜" |

The steps of adding USP Standard purified water to Avitene® flour, then lyophilizing this slurry, changes the physical appearance of the Avitene® flour from a loose flour like powder to a solid, pliable light weight foam. This affects the physical appearance of the collagen but the chemical composition remains the same as that of Avitene® flour. Because the added steps do not change the chemical composition of the microfibrillar structure of the collagen, the mode of action and hemostatic characteristics of the collagen foam are preserved.

To control bleeding, Ultrafoam™ typically is cut to the desired size and applied directly to the source of bleeding. The Ultrafoam™ is held in place with moderate pressure until hemostasis results. The period of time to hold pressure on the foam will vary with the force and severity of bleeding. Ultrafoam™ may be left in place at the bleeding site when necessary. Prior to removal, the foam should be moistened with saline to avoid dislodging the clot.

Manufacturing Process

The process to make a foam product involves the addition of USP water to Avitene® Bulk Flour and removing the water via a lyophilization (freeze drying) process. The following is an overview of the process and steps used in the Manufacture, Quality Control and Test Procedures, for this preferred embodiment.

In general Avitene® bulk flour is mixed with USP purified water, poured into trays and lyophilized. After processing, it is inspected and released to manufacturing and staged for the cleanroom.

In the clean rooms, the first step is skiving, a process of removing the surface layer of the material with a machine known as a band knife splitter, to remove the "skin" formed on the surface during the lyophilization process and then slicing the material to the proper thickness. After skiving, the pieces are transferred to the cutting operation where the pieces are cut to the appropriate size.

After cutting, the Ultrafoam™ pieces are placed into individual polycarbonate trays which are then sealed with a tyvek lid. This packaged unit is then placed onto a cart and run through a Despatch Index drying oven wherein it is dried to a specific moisture content. After drying, the sealed polycarbonate trays are placed into PET/nylon/foil laminate pouches which are heat sealed and the pieces are transferred to the sterilization operation. The sterilization employed is dry heat, 126° C. at 20 hours. Upon completion of sterilization the material is packaged and labeled into cartons after which it is held in quarantine until it is released to distribution.

A detailed description of each of the major steps of the process, namely, mixing, lyophilization, cutting/skiving/packaging and sterilization, and final packaging is presented below.

Mixing: The Avitene Bulk Flour is mixed with USP Purified Water at 13.9 grams of flour per 1.00 Liter USP water using a peristaltic pump at the highest setting for approximately one and one half hours to ensure a percent solids of 1.37% (nominal) as determined during the initial development phase of the product.

Early in the concept development phase of the foam product, studies were completed to determine the desired formulation for the foam. The studies examined the effects of percent collagen (ratio of collagen to USP water), collagen fiber length (nominal and shortened), dwell time between mixing and lyophilizing, and various cross-linking methods (heat sterilization, gamma sterilization, electron beam exposure and chemical cross-linking agents) on the foam. Foam product was made with various combinations of the aforementioned variables. Based on physical testing and evaluations of prototype units, the key factors for production of the foam were defined as the ratio of collagen to water, fiber length and cross-linking method. These factors were optimized to be 13.9 grams of flour/liter of USP water (with a range of 11.1–16.7 grams of flour/liter of USP water), nominal Avitene flour fiber length and heat sterilization/cross-linking. The dwell time between mixing and lyophilizing was determined to not significantly influence the product, as long as it did not exceed 27 hours (the maximum dwell time examined in the study).

Once the ratio of Avitene flour to USP water was defined, a mixing process was developed to ensure that the collagen was evenly distributed throughout the flour/water mixture to provide for a uniform percent solids. A peristaltic pump was used to accomplish the mixing in a manner as to not compromise the fiber length of the flour (low shear). The mixing is performed for approximately 90 minutes with the pump set to its highest setting in a stainless steel vessel. The percent solids for the mixture preferably is in the range of about 1.10% to about 1.64% solids.

Lyophilization: After mixing the product is transferred into stainless steel trays which are approximately 12×36 inches and put into the lyophilizer where it is exposed to a lyophilization cycle of temperature of 5.9° C./hour, 36° C. terminal temperature for 38 hours and 100 mT (milliTorr) vacuum to obtain a foam product.

The foam product is inspected for thickness, density and general appearance. Once acceptable, it is released for manufacturing and staged for the clean room, where it undergoes the following manufacturing steps:

Skiving Process: The material is received from the lyophilization process in sheets which are approximately 12 by 36 inches. These sheets are fed into the bandknife splitter via rollers set at a given distance from the center blade (stainless steel) which removes the "skin" layer formed during the lyophilization process. In some cases, multiple passes of the material are made through the machine until the proper thickness is achieved.

Cutting Process: After skiving, the material is transferred to the cutting station where the skived pieces are put through a cutting machine consisting of a stainless steel rotary blade cutter an indexing station which cuts the pieces to size. After the skiving and cutting operations the pieces are inspected for proper dimensions (length, width, thickness), percent moisture and general appearance and are then released to the next operation, the drying step.

Packaging and drying process: The packaging and drying step is a continuous process of packaging into polycarbonate trays and sealing with tyvek lid, loading the sealed units onto carts and then placing them into the Despatch Index Drying Oven where they are exposed to a cycle of 110° C. for approximately 2 hours to reduce the moisture level in the product to 4%.

During the drying process, samples are taken from every cart to confirm that the moisture content of the product is 4% or less. If acceptable, the product is removed and sent to the second stage of packaging, foil pouching. If the products do not meet the moisture specification after a single exposure to the drying cycle additional testing will be performed to determine if the product can withstand exposure to two drying cycles without detriment to the product or package. Once dry, the product is placed into PET/nylon/foil laminated pouches and heat sealed.

Example 2

Assay for Determining Tensile Strength

This assay is performed to determine the tensile strength of a hemostatic device of the invention formed of Avitene® flour (Ultrafoam™) and compare its tensile strength to that of a Gelfoam® control. The foam samples were tested in the tensile direction using a dog bone shape sample. Foam samples were tested for tensile properties in the wet state using an Instron® Tensile Tester with Flat Face Grips, beaker, calipers, de-ionized Water (room temperature), 1"×2" Bone-shaped Steel Roll Die (0.5" wide at the center), Clicker Press, Gelfoam®, Product Code: 100, and Ultrafoam™.

The Ultrafoam™ that was used for the testing was produced by mixing a slurry (Avitene® powder and water—1.25% w/v) using a mechanical mixer (variable speed, electrical stirrer with twin propellers). The slurry was mixed for 24 hours. The finished slurry still had small clumps of collagen in the mixture. The mixing was not a thorough process, but was sufficient for concept testing. The slurry was put into 4 L jars and lyophilized. Once lyophilized, the foam was placed into aluminum foil (loosely packaged) and put through a sterilization process of 125° C. for 22 hours. The foam was then ready for testing. The Gelfoam® was die cut using the clicker press and the bone-shaped steel roll die; 10 total bone-shaped pieces of Gelfoam® were cut for testing and 30 pieces of Ultrafoam™ were cut as well. Samples were placed in a beaker of de-ionized water, keeping both the Gelfoam® and Ultrafoam™ separated. The air trapped within the samples was removed by kneading the samples (only necessary with the Gelfoam® samples).

The gauge length of the grips on the Instron® Tensile Tester was set to 1 inch. The first Gelfoam® sample was placed in the grips and closed using the foot-pedal. The sample thickness was measured using the calipers and recorded for the sample on the computer. The samples were run at a crosshead speed of 12 in/min in the tensile direction.

The following data for each sample was recorded: Maximum Load (lbs.); Strain at Break (%); Secant Modulus (psi); Energy at Maximum Load (psi). The procedure was repeated for the rest of the Gelfoam® samples. The procedure was then repeated to test the Ultrafoam™ samples.

The Gelfoam® samples were immersed in water for two hours and were kneaded to remove excess air trapped within the samples (to fully hydrate the samples). The Gelfoam® samples did not hydrate quickly. The tensile properties for the maximum load of the samples ranged from 0.15 to 0.23 pounds force with a mean of 0.17 pounds. The standard deviation was 0.02 pounds.

The Ultrafoam™ samples did not require kneading to remove air; however kneading was performed to be consistent with the treatment of the Gelfoam® samples. The Ultrafoam™ samples did not required extensive soak time; they immediately wicked to become fully hydrated. The tensile properties for the maximum load of the samples ranged from 0.13 to 0.20 pounds force. The mean was 0.16 pounds with a standard deviation of 0.03 pounds force.

The Ultrafoam™ samples were equivalent to the Gelfoam® samples for maximum load in the tensile direction. The hydrating properties of the Ultrafoam™ were much quicker (within 2 minutes) than the Gelfoam® samples (over two hours).

Example 3

Assay for Determining Density

This assay is performed to determine the density of dry Ultrafoam™ for both pre and post sterility samples. The equipment used included: digital calipers, square or rectangle steel roll die, flat plexiglass, rubber mallet, top-loading scale (able to measure to at least 0.001 grams).

Samples for testing were die cut from the above-described foam using the steel roll die by placing the foam over the die. Next, a piece of flat plexiglass (big enough to cover the die) was placed on top of the foam and, by using the rubber mallet to gently tap the plexiglass, a shape of foam was cut out from the foam. This procedure was repeated until the number of samples needed were cut to shape.

The digital calipers were used to measure the length (L), width (W) and thickness (T) (at least three measurements were made of each dimension and the average of the measurements was used). The average measurement of the sample's dimensions was recorded and the sample was placed on the scale to obtain the sample weight of the sample which was then recorded. This procedure was repeated until all samples were measured.

If dimensional measurements were measured in units of inches, inches (in) was converted to centimeters (cm) and the conversions were recorded in centimeter units. The following calculation was used to determine the density of the foam sample(s):

$$\text{Density} = [wt(g)/(L(cm)*W(cm)*T(cm))]$$

and the density results were recorded in units of grams per cubic centimeter (g/cc) of each sample.

Example 4

Comparison of Hemostatic Activity Between Ultrafoam™ AND Gelfoam®

Test Method

The hemostatic response time of Ultrafoam™ (Lot 081398) with and without thrombin, was compared to Gelfoam® (Lot 40CAR, with and without thrombin) in a pig spleen model (J&J Hemostasis protocol) as follows. Small incisions were made in the retracted spleen of anesthetized juvenile Yorkshire pigs. The number of cuts per spleen ranged from 8 to 18. Eight pigs were required. Thrombin was added to the device by soaking the sample in a thrombin solution until fully saturated. The test device (approximately 0.5"×0.5") was placed on the wound, tamponaded with finger pressure for 20 seconds, then the pressure was removed and the site was observed for re-bleed for two minutes. If re-bleed was observed within two minutes, pressure was reapplied for 20 seconds and the cycle was repeated. The endpoint of the hemostatic assay is the number of tamponades to achieve no re-bleed. The following samples were paired during testing (20 pairs each): Ultrafoam™ versus Gelfoam®, Ultrafoam™ versus Gelfoam®-thrombin, Ultrafoam™-thrombin versus Gelfoam®-thrombin. A pair was defined as two samples tested one after the other and adjacent to one another on the spleen. For each pair, the first sample tested was alternated from pair to pair. Each pair was tested at least once, usually twice, and sometimes 3 times on each animal to better characterize animal to animal variability.

Statistical Methods

The frequency of the number of tamponades for each product type within the paired group, was analyzed using the Fisher's exact test and the Stuart-Maxwell test (both one-tailed) at alpha 0.05. It was expected that Ultrafoam™ without thrombin would need fewer tamponades than Gelfoam® without thrombin, but would require more tamponades than Gelfoam® with thrombin. These paired groups were analyzed separately. Therefore, a one-sided test based on expected results was appropriate.

The SAS software package was used for calculating the Fisher's exact test for each paired group. For n×n ("×" means multiplication) contingency tables (foam type× number of tamponades), Fisher's exact test yields the probability of observing a table that gives at least as much evidence of association as the one actually observed, given that the null hypothesis is true. The hypergeometric probability (p value) of every possible table is computed (from the SAS/STAT User's Guide, release 6.03 edition). If ½×the two-tailed p value (which is the one-tailed p value) was less than or equal to 0.05, the frequency distributions were considered significantly different.

The Stuart-Maxwell test, which is a generalization of the McNemar test, was normally calculated using Table 8.5 and formulas 8.18 and 8.19 on page 120 of "Statistical Methods for Rates and Proportions," Joseph L. Fleiss, 2nd edition, published by John Wiley & Sons, New York, N.Y. The Stuart-Maxwell test involves determining the number of pairs with the same result and differing results, and calculating the value of the Stuart-Maxwell chi-square at 2 degrees of freedom for matched pairs with 3 mutually exclusive outcomes. The one-tailed alpha value was 0.10 (two-tailed value of 0.05×2). For the purposes of this calculation, the 3 outcomes were 1, 2, or 3 tamponades. In 2 cases (1 Gelfoam® without thrombin and 1 Ultrafoam™ without thrombin) a sample that required 4 tamponades was treated as a 3 in order to allow the use of the Stuart-Maxwell test.

Results

Overall, the animal model worked well for the comparison of hemostatic response time. The tamponade method was representative of actual product use. All product samples tested were considered adequate hemostats with differing degrees of performance.

The frequency (%) of Ultrafoam™ samples requiring 1, 2, 3, or 4 tamponades in the Ultrafoam™/Gelfoam®-thrombin pairs was 80, 15, 0, and 5 respectively. Gelfoam®-thrombin exhibited 85, 15, 0, and 0 respectively. Both frequency distributions were skewed to 1 tamponade. There was no significant difference between the Ultrafoam™ and Gelfoam®-thrombin tamponade frequency distributions according to both the Fisher's exact test (one-sided p value>=0.500) and the Stewart-Maxwell test (one sided p value>=0.303). This result was important because it indicated that in this model, Ultrafoam™ did not require thrombin to be as effective as Gelfoam® with thrombin.

In the Ultrafoam™-thrombin/Gelfoam®-thrombin pairs, the frequency of Ultrafoam™-thrombin samples requiring 1, 2, 3, or 4 tamponades was 80, 10, 5, and 0 respectively. Gelfoam®-thrombin exhibited 85, 15, 0, and 0 respectively. Both frequency distributions were skewed to 1 tamponade. There was no significant difference between the Ultrafoam™-thrombin and Gelfoam®-thrombin tamponade frequency distributions according to both Fisher's exact test (one-sided p value>=0.500) and the Stewart-Maxwell test (one sided p value>=0.274). This result was important because it indicated that in this model, Ultrafoam™ was compatible with thrombin and thrombin did not react synergistically with Ultrafoam™.

Figure 2:
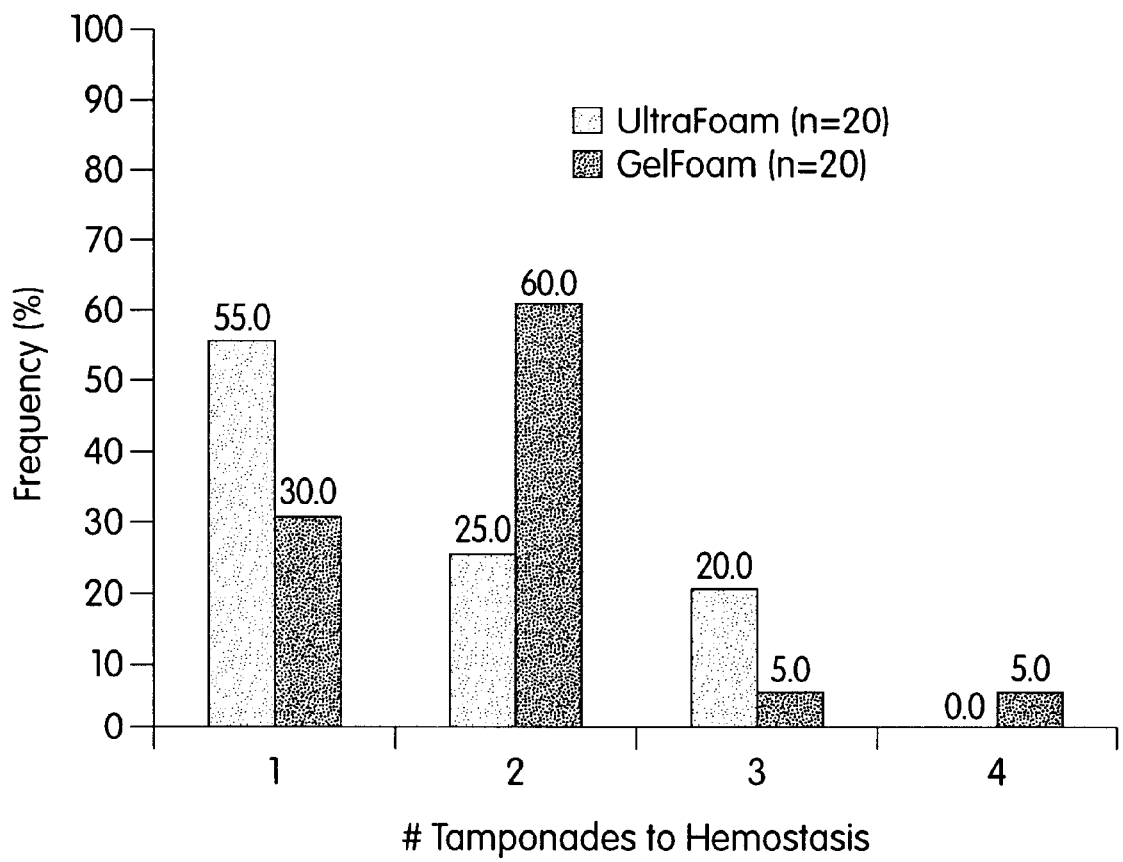
FIG. 2 shows the hemostatic responses for a hemostatic device of the invention (referred to as Ultrafoam™) compared to Gelfoam®, indicating that Ultrafoam™ without thrombin performed significantly better than Gelfoam® without thrombin.

In the Ultrafoam™ vs. Gelfoam® pairs, the frequency of Ultrafoam™ samples requiring 1, 2, 3, or 4 tamponades was 55, 25, 20, and 0 respectively (FIG. 2). Gelfoam® exhibited 30, 60, 5, and 5 respectively (FIG. 2). The Ultrafoam™ distribution was skewed to 1 tamponade. The Gelfoam® distribution was skewed to 2 tamponades. The tamponade frequency distribution for Ultrafoam™ was significantly different than the tamponade frequency distribution for Gelfoam® according to the Fisher's exact test (one-sided p value>=0.035). The Stewart-Maxwell test indicated the tamponade frequency distributions were borderline s significantly different (one-sided p value>=0.054). This result was important because it indicated that in this model, Ultrafoam™ without thrombin performed significantly better than Gelfoam® without thrombin.

The percentage (55%) for 1 tamponade for the Ultrafoam™ samples in the Ultrafoam™/Gelfoam® pairs was lower than the percentage (80%) for 1 tamponade for the Ultrafoam™ in the Ultrafoam™/Gelfoam®-thrombin pairs. The only experimental factor that could be found that could account for this difference was the timing of scalpel blade changes. A large percentage (70%) of the pairs in the Ultrafoam™/Gelfoam® group were tested on spleen cuts made with a fresh scalpel blade. None of the pairs in the Ultrafoam™/Gelfoam®-thrombin group were tested on spleen cuts made with a fresh scalpel blade. The comparison of Ultrafoam™ to Gelfoam® was valid, since both samples were tested on approximately the same number of spleen cuts made with fresh scalpel blades. Therefore, the variability that may have been introduced by the timing of scalpel blade changes, did not meaningfully affect the paired results.

DISCUSSION

Overall, the tamponade frequency distributions were similar for all samples with the exception of Gelfoam® without thrombin. Ultrafoam™ without thrombin, Ultrafoam™ with thrombin, and Gelfoam® with thrombin all exhibited tamponade frequency distributions that were skewed to 1 tamponade. The fact that Ultrafoam™ without thrombin performed comparably to Gelfoam® with thrombin was clearly an important finding. Extrapolating from the animal model to the clinical situation, clinical users may choose to use Ultrafoam™ in the dry state without thrombin, saving time and money, since only one product would be used instead of two. The soft and flexible handling characteristics of Ultrafoam™ will allow it to be used in the dry state.

Gelfoam® without thrombin exhibited a tamponade frequency distribution that was skewed to 2 tamponades, whereas Ultrafoam™ without thrombin was skewed to 1 tamponade.

In this study, one statistical analysis method determined that the two distributions were different, and a second method determined they were not different, although this second test was borderline. However, the data certainly suggest that Ultrafoam™ exhibited increased hemostatic performance compared to Gelfoam®. The increased hemostatic activity of Ultrafoam™ without thrombin compared to Gelfoam® without thrombin was an unexpected outcome because Ultrafoam is composed of active microfibrillar collagen whereas Gelfoam® is composed of inactive collagen or gelatin. In addition, Ultrafoam™ absorbs fluid more quickly than Gelfoam®, and will quickly absorb blood and stimulate the clotting cascade.

The data in this study indicated that Ultrafoam™ with and without thrombin was an effective hemostat, comparable and, in some instances, exceeding the industry standard Gelfoam®-thrombin.

TABLE 1

Frequency (%) of number of tamponades.

| Product | Number of Tamponades | | | |
|---|---|---|---|---|
| N = 20 pairs | 1 | 2 | 3 | 4 |
| Ultrafoam ™-thrombin/Gelfoam ® Pairs | | | | |
| Ultrafoam ™ | 80 | 15 | 0 | 5 |
| Gelfoam ®-thrombin | 85 | 15 | 0 | 0 |
| Ultrafoam ™-thrombin/Gelfoam ®-thrombin Pairs | | | | |
| Ultrafoam ™-thrombin | 85 | 10 | 5 | 0 |
| Gelfoam ®-thrombin | 85 | 15 | 0 | 0 |
| Ultrafoam ™-Gelfoam ® Pairs | | | | |
| Ultrafoam ™ | 55 | 25 | 20 | 0 |
| Gelfoam ® | 30 | 60 | 5 | 5 |

TABLE 2

Number of pairs for each outcome for Ultrafoam ™/Gelfoam ®-thrombin pairs.

| Ultrafoam ™ | Gelfoam ™-Thrombin Number of Tamponades | | | |
|---|---|---|---|---|
| Number of Tamponades | 1 | 2 | 3 | Total |
| 1 | 14 | 2 | 0 | 16 |
| 2 | 2 | 1 | 0 | 3 |
| 3 | 1* | 0 | 0 | 1 |
| Total | 17 | 3 | 0 | 20 |

*Note: One Ultrafoam ™ sample required 4 tamponades, but was re-classed to 3 tamponades to allow calculation of The Stewart-Maxwell statistic.

TABLE 3

Number of pairs for each outcome for
Ultrafoam ™-thrombin/Gelfoam ®-thrombin pairs

| Ultrafoam ™ thrombin | Gelfoam ™-Thrombin Number of Tamponades | | | |
|---|---|---|---|---|
| Number of Tamponades | 1 | 2 | 3 | Total |
| 1 | 14 | 3 | 0 | 17 |
| 2 | 2 | 0 | 0 | 2 |
| 3 | 1 | 0 | 0 | 1 |
| Total | 17 | 3 | 0 | 20 |

TABLE 4

Number of pairs for each outcome for Ultrafoam ™/Gelfoam ® pairs

| Ultrafoam ™ | Gelfoam ® Number of Tamponades | | | |
|---|---|---|---|---|
| Number of Tamponades | 1 | 2 | 3 | Total |
| 1 | 4 | 7 | 0 | 11 |
| 2 | 1 | 3 | 1* | 5 |
| 3 | 1 | 2 | 1 | 4 |
| Total | 6 | 12 | 2 | 20 |

*Note: One Gelfoam sample required 4 tamponades, but was re-classed to 3 tamponades to allow calculation of the Stewart-Maxwell statistic.
All of the references, patents and patent publications identified or cited herein are incorporated, in their entirety, by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed:

1. A process for preparing a hemostatic device, comprising:
   (a) suspending a plurality of collagen particles in water to form a collagen slurry, wherein the collagen particles have a bulk density sufficient to form a suspension in water and wherein the collagen slurry has a collagen concentration in the range of about 1% to about 2% (weight/volume); and
   (b) lyophilizing the collagen slurry to form a hemostatic device.

2. The process of claim 1, wherein the collagen particles comprise collagen fibrils.

3. The process of claim 1, wherein the collagen particles have a bulk density in the range of about 1.5 lbs/ft$^3$ to about 3.5 lbs/ft$^3$.

4. The process of claim 1, wherein the process comprises the further step of:
   introducing the collagen slurry into a mold prior to lyophilizing the collagen slurry.

5. The process of claim 1, wherein the process further comprises the step of crosslinking the hemostatic device to form a crosslinked-hemostatic device.

6. The process of claim 1, comprising the further step of introducing a hemostatic agent into one or both of the collagen slurry and the hemostatic device.

7. The process of claim 1, comprising the further step of introducing thrombin into one or both of the collagen slurry and the hemostatic device.

8. The process of claim 1, comprising the further step of removing a surface layer of the hemostatic device.

9. A hemostatic device prepared by the process comprising:
   (a) suspending a plurality of collagen particles in water to form a collagen slurry, wherein the collagen particles have a bulk density sufficient to form a suspension in water and wherein the collagen slurry has a collagen concentration in the range of about 1% to about 2% (weight/volume); and
   (b) lyophilizing the collagen slurry to form a hemostatic device.

10. The product of claim 9, wherein the collagen particles comprise microfibrillar collagen.

11. The product of claim 9, wherein the collagen particles have a bulk density in the range of about 1.5 lbs/ft$^3$ to about 3.5 lbs/ft$^3$.

12. The product of claim 9, wherein the process comprises the further step of introducing the collagen slurry into a mold prior to lyophilizing the collagen slurry.

13. The product of claim 9, wherein the process further comprises the step of crosslinking the hemostatic device to form a crosslinked-hemostatic device.

14. The product of claim 9, wherein the process further comprises the step of removing a surface layer of the hemostatic device.

15. The product of claim 9, wherein the process further comprises the step introducing into the hemostatic device, a hemostasis-promoting amount of at least one hemostatic agent effective to accelerate clot formation at an interface between a wound surface and the hemostatic device.

16. The product of claim 9, wherein the process further comprises the step introducing into the hemostatic device, a therapeutically-effective amount of at least one therapeutic agent.

17. A sterile package containing the hemostatic device of claim 9.

18. A method for promoting hemostasis comprising, manually pressing the hemostatic device of claim 9 against a bleeding surface for a period of time until clotting has occurred at the interface between the hemostatic device and the surface.

19. A hemostatic device, wherein the collagen particles of the hemostatic device have a hemostatic activity that is equivalent to the hemostatic activity of the collagen particles from which the hemostatic device is formed.

20. The hemostatic device of claim 19, wherein the hemostatic device is a foam.

21. The hemostatic device of claim 19, wherein the hemostatic device does not contain thrombin and the hemostatic device has a hemostatic activity in a pig spleen animal model that is greater than that of Gelfoam® with thrombin.

22. The hemostatic device of claim 19, wherein the hemostatic device has a thickness of about ⅜ inch and an acute maximum load of greater than or equal to 0.08 lbs.

23. The hemostatic device of claim 19, wherein the hemostatic device is dry and has a modulus of less than or equal to 86 psi.

24. The hemostatic device of claim 19, wherein the hemostatic device has a wettability index of less than or equal to 1 minute in distilled water at room temperature.

25. The hemostatic device of claim 19, further comprising a hemostasis-promoting amount of at least one hemostatic agent effective to accelerate clot formation at an interface between a wound surface and the hemostatic device.

26. The hemostatic device of claim 19, further comprising a therapeutically-effective amount of at least one therapeutic agent.

27. The hemostatic device of claim 19, further comprising a hemostasis-promoting amount of at least one hemostatic agent effective to accelerate clot formation at an interface between a wound surface and the hemostatic device.

28. A sterile package containing a hemostatic device of claim 19.

29. A method for promoting hemostasis comprising, manually pressing a hemostatic device of claim 19 against a bleeding surface for a period of time until clotting has occurred at the interface between the hemostatic device and the surface.

30. A hemostatic device comprising collagen, wherein the hemostatic device has a hemostatic activity in a pig spleen animal model of hemostasis that corresponds to one tamponade for a hemostatic device having a thickness of ⅜ inch, a length of ½ inch, and a width of ½ inch.

31. The hemostatic device of claim 30, wherein the hemostatic device does not contain thrombin and the hemostatic device has a hemostatic activity in a pig spleen animal model that is greater than that of Gelfoam® with thrombin.

32. The hemostatic device of claim 30, wherein the hemostatic device has a density in the range of about 0.015 to about 0.023 gm/cc.

33. The hemostatic device of claim 30, wherein the hemostatic device has a weight percent solids in the range of about 1.10 to about 1.64 weight percent.

34. The hemostatic device of claim 30, wherein the hemostatic device has a thickness of about ⅜ inch and an acute maximum load of greater than or equal to 0.08 lbs.

35. The hemostatic device of claim 30, wherein the hemostatic device is dry and has a modulus of less than or equal to 86 psi.

36. The hemostatic device of claim 30, wherein the hemostatic device has a wettability index of less than or equal to 1 minute in distilled water at room temperature.

37. The hemostatic device of claim 30, further comprising a hemostasis-promoting amount of at least one hemostatic agent effective to accelerate clot formation at an interface between a wound surface and the hemostatic device.

38. The hemostatic device of claim 30, further comprising a therapeutically-effective amount of at least one therapeutic agent.

39. A hemostatic device comprising collagen, wherein the hemostatic device is dry and sufficiently flexible to conform to the contours of a biological surface and absorb exudants present at the biological surface, and wherein the collagen has not been subjected to acid dissolution.

40. A process for preparing a hemostatic device, comprising:
(a) suspending a plurality of collagen particles in water to form a collagen slurry, wherein the collagen particles have a bulk density sufficient to form a suspension in water and wherein the collagen slurry has a collagen concentration in the range of about 1% to about 2% (weight/volume);
(b) introducing the collagen slurry into a mold; and
(c) lyophilizing the collagen slurry to form a hemostatic device.

41. A process for preparing a hemostatic device, comprising:
(a) suspending a plurality of collagen particles in water to form a collagen slurry, wherein the collagen particles have a bulk density sufficient to form a suspension in water and wherein the collagen slurry has a collagen concentration in the range of about 1% to about 2% (weight/volume);
(b) lyophilizing the collagen slurry to form a hemostatic device; and
(c) removing a surface layer of the hemostatic device.

42. A hemostatic device prepared by the process comprising:
(a) suspending a plurality of collagen particles in water to form a collagen slurry, wherein the collagen particles have a bulk density sufficient to form a suspension in water and wherein the collagen slurry has a collagen concentration in the range of about 1% to about 2% (weight/volume);
(b) introducing the collagen slurry into a mold; and
(c) lyophilizing the collagen slurry to form a hemostatic device.

43. A hemostatic device prepared by the process comprising:
(a) suspending a plurality of collagen particles in water to form a collagen slurry, wherein the collagen particles have a bulk density sufficient to form a suspension in water and wherein the collagen slurry has a collagen concentration in the range of about 1% to about 2% (weight/volume);
(b) lyophilizing the collagen slurry to form a hemostatic device; and
(c) removing a surface layer of the hemostatic device.

44. A hemostatic device, wherein the collagen particles of the hemostatic device have a hemostatic activity that is equivalent to the hemostatic activity of the collagen particles from which the hemostatic device is formed,
wherein the hemostatic device does not contain thrombin and the hemostatic device has a hemostatic activity in a pig spleen animal model that is greater than that of Gelfoam® with thrombin.

45. A hemostatic device, wherein the collagen particles of the hemostatic device have a hemostatic activity that is equivalent to the hemostatic activity of the collagen particles from which the hemostatic device is formed,
wherein the hemostatic device has a wettability index of less than or equal to 1 minute in distilled water at room temperature.

* * * * *